United States Patent [19]  [11] 3,989,744
Woessner et al. [45] Nov. 2, 1976

[54] 11-SUBSTITUTE D-11-DESOXY-PGE ANALOGUES

[75] Inventors: Warren Dexter Woessner; Henry Clifford Arndt; William Gerard Biddlecom, all of Madison; George Peter Peruzzotti, Middleton; Charles John Sih, Madison, all of Wis.

[73] Assignee: Miles Laboratories, Inc., Elkhart, Ind.

[22] Filed: July 30, 1973

[21] Appl. No.: 384,075

[52] U.S. Cl. .......................... 260/514 D; 260/468 D; 260/473 R; 260/473 G; 260/520 B; 424/305; 424/308; 424/317
[51] Int. Cl.² .................. C07C 61/38; C07C 69/74; C07C 65/14; C07C 65/22
[58] Field of Search ............ 260/468, 514, 473, 520

[56] References Cited
UNITED STATES PATENTS
3,845,042   10/1974   Strike et al. ..................... 260/240

FOREIGN PATENTS OR APPLICATIONS
7,311,403   2/1974   Netherlands ..................... 260/465

OTHER PUBLICATIONS
Grudzinskas et al., Tet. Letters, 141 (1973).

Primary Examiner—Robert Gerstl
Attorney, Agent, or Firm—Myron B. Sokolowski

[57] ABSTRACT

11-Substituted-11-desoxy-PGE and -PGF analogues, in which the 11-substituent may be phenyl, (substituted)phenyl, cycloalkyl, spiroalkyl, branched or linear alkyl and alkenyl, and 3-hydroxy-alkenyl, stimulate smooth muscle.

3 Claims, No Drawings

11-SUBSTITUTE D-11-DESOXY-PGE ANALOGUES

BACKGROUND OF THE INVENTION

Field of the Invention

The compounds of this invention are derivatives or analogues of a class of naturally occurring chemical compositions known as prostaglandins.

Natural prostaglandins are twenty-carbon atom alicyclic compounds related to prostanoic acid which is represented by the following structural formula:

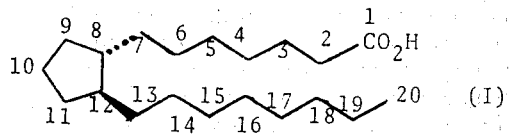

By convention, the carbon atoms of I are numbered sequentially from the carboxylic carbon atom. An important stereochemical feature of I is the trans-orientation of the side chains $C_1$–$C_7$ and $C_{13}$–$C_{20}$. In I, as elsewhere in this specification, a dotted line (....) indicates projection of the covalent bond below the plane of a reference carbon atom (the alpha-configuration), while a wedged line (◄) represents direction above said plane (the beta-configuration). These notations are applicable to all compounds hereinafter discussed.

The twelve natural prostaglandins which have been isolated to date have the structural formula:

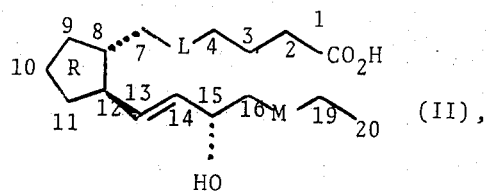

in which:

L and M may be ethylene or vinylene radicals; and, the five-membered ring

The natural prostaglandins represented by II, are classified according to the functional groups present in the five-membered ring structure and the presence of double bonds in the ring or chains. Prostaglandins of the F-class (PGF's) are characterized by α-oriented hydroxyl groups at $C_9$ and $C_{11}$; those of the E-type (PGE's) have a carbonyl group at $C_9$ and an α-oriented hydroxyl group at $C_{11}$; compounds of the A-series (PGA's) contain a carbonyl group at $C_9$ and a double bond at $C_{10}$ ($\Delta^{10,11}$); and members of the B-class (PGB's) have a carbonyl group at $C_9$ and unsaturated bond between $C_8$ and $C_{12}$ ($\Delta^{8,12}$). Within each of the F, E, A, and B classes of prostaglandins are three subclassifications based upon the presence of double bonds in the side chains at $C_5$, $C_{13}$, or $C_{17}$. The presence of a trans-unsaturated bond only at $C_{13}$ is indicated by the subscript numeral 1; thus, for example, $PGE_1$ denotes a prostaglandin of the E-type (carbonyl at $C_9$ and an alpha-hydroxyl at $C_{11}$) with a trans-double bond at $C_{13}$. The presence of both a trans-double bond at $C_{13}$ and a cis-unsaturated bond at $C_5$ is denoted by the subscript numeral 2, for example, $PGE_2$. Lastly, a trans-double bond at $C_{13}$, a cis-double bond at $C_5$, and a cis-double bond at $C_{17}$ is indicated by the subscript numeral 3, for example, $PGE_3$. The above notations apply to prostaglandins of the A, B and F series as well, however, in the latter the alpha-orientation of the hydroxyl group at $C_9$ is indicated by the subscript Greek letter α after the numerical subscript. Thus $PGF_{3\alpha}$ represents 9α,1-1α,15α-trihydroxy-5,17-cis, 13-trans-prostatrienoic acid (utilizing nomenclature based upon prostanoic acid).

It is important to note that in all natural prostaglandins there is an alpha-oriented hydroxyl group at $C_{15}$. In the Cahn-Ingold-Prelog system of defining stereochemistry, this $C_{15}$ hydroxyl group is in the S-configuration.

11-desoxy derivatives of PGE and PGF molecules do not occur as such in nature, but constitute a class of compounds which possess biological activity related to the parent compounds. Formula II represents 11-desoxy PGE's and PGF's when

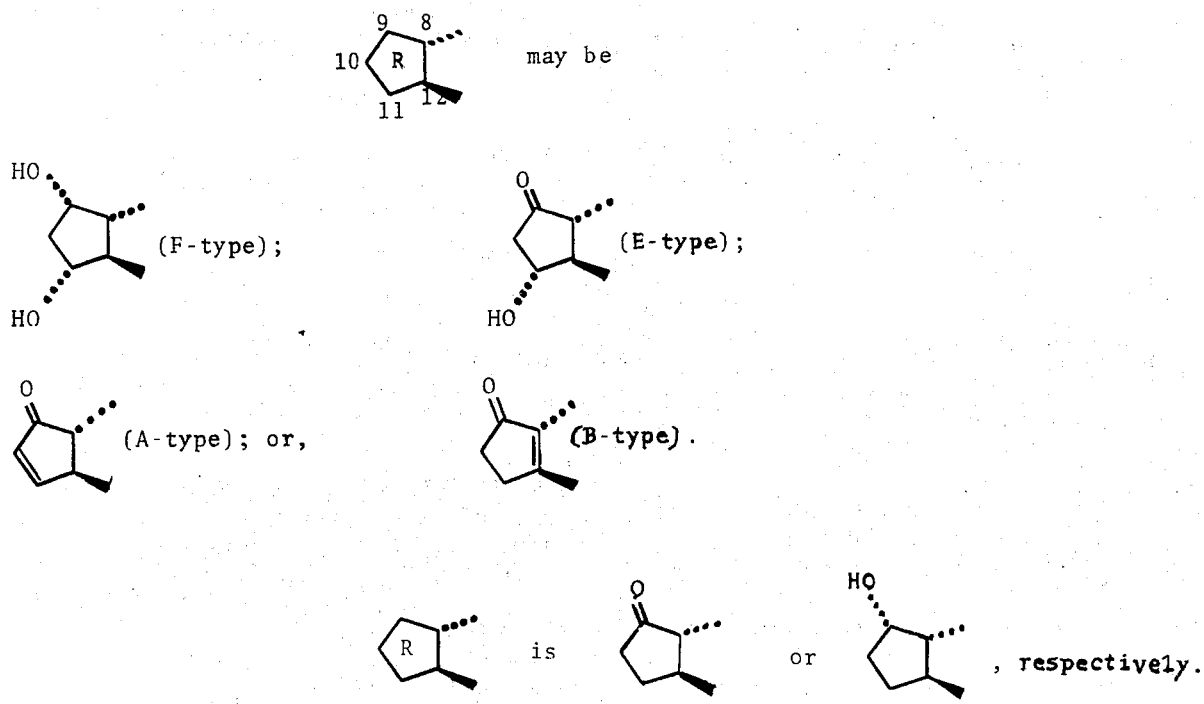

I.U.P.A.C nomenclature of prostaglandins designates the carboxylic side chain as the parent compound: for example, $PGF_{3\alpha}$ is 7-{3α, 5α-dihydroxy-2β-[(3S)-3-hydroxy-trans-1, Cis-5-octenyl]-1α-cyclopentyl}-cis-5-heptenoic acid.

Recent research has indicated that the prostaglandins are ubiquitous in animal tissues and that prostaglandins, as well as analogues or derivatives thereof, have important biochemical and physiological effects in mammalian endocrine, reproductive, central and peripheral nervous, sensory, gastro-intestinal, hematic, respiratory, cardiovascular, and renal systems.

In mammalian endocrine systems, experimental evidence indicates prostaglandins are involved in the control of hormone synthesis and release in hormone-secreting glands. In rats, for example, $PGE_1$ and $PGE_2$ increase release of growth hormone while $PGA_1$ increases growth hormone synthesis. In sheep, $PGE_1$ and $PGF_{1\alpha}$ inhibit ovarian progesterone secretion. In a variety of mammals, $PGF_{1\alpha}$ and $PGF_{2\alpha}$ are implicated as luteolytic factors. In mice, $PGE_1$, $PGE_2$, $PGF_{1\alpha}$ and $PGE_{1\beta}$ increase thyroid activity. In hypophysectomized rats, $PGE_1$, $PGE_2$ and $PGF_{1\alpha}$ stimulate steroidogenesis in the adrenal glands.

In the mammalian male reproductive system, $PGE_1$ contracts the smooth muscle of the vas deferens. In the female reproductive system, PGE and $PGF\alpha$ compounds contract uterine smooth muscle. In general, PGE's, PGB's and PGA's relax in vitro human uterine muscle strips, while $PGF\alpha$'s contract such isolated preparations. PGE compounds in general promote fertility in the female reproductive system while $PGF_{2\alpha}$ has antifertility effects. $PGF_{2\alpha}$ also is believed to be involved in the mechanism of menstruation. In general, $PGE_2$ exerts potent oxytocic effects in inducing labor, while $PGF_{2\alpha}$ induces spontaneous abortions in early pregnancy.

$PGF_\alpha$'s and PGE's have been isolated from a variety of nervous tissue and they have been postulated to serve a neurotransmitter role. $PGE_1$ retards whereas $PGF_{2\alpha}$ facilitates transmission in motor pathways in the CNS. It has been reported that $PGE_1$ and $PGE_2$ inhibit transmitter release from adrenergic nerve endings in the guinea pig.

Prostaglandins stimulate contraction of gastrointestinal smooth muscle in vivo and in vitro. In dogs, $PGA_1$, $PGE_1$ and $PGE_2$ inhibit gastric secretion. $PGA_1$ exhibits similar activity in man.

In most mammalian respiratory tracts, PGE's and $PGF_\alpha$'s relax in vitro preparation of tracheal smooth muscle. In in vitro preparations, $PGE_1$ and $PGE_2$ relax human smooth muscle while $PGF_{2\alpha}$ contracts such preparations. PGE and PGF compounds are normally found in the human lung, and it has been postulated that some cases of bronchial asthma involve an imbalance in the production or metabolism of those compounds.

Prostaglandins have been shown to be involved in certain hematic mechanisms in mammals. $PGE_1$, for example, inhibits thrombogenesis in vitro through its effects on blood platelets.

In a variety of mammalian cardiovascular systems, PGE's and PGA's are vasodilators whereas $PGF_\alpha$'s are vasoconstrictors, by virtue of their action on vascular smooth muscle.

Prostaglandins are naturally found in the kidney and reverse experimental and clinical renoprival hypertension.

The clinical implications of prostaglandins and derivatives or analogues thereof are far-ranging and include, but are not limited to the following: in obstetrics and gynecology, they may be useful in fertility control, treatment of menstrual disorders, induction of labor, and hormone disorders; in gastroenterology, they may be useful in the treatment of peptic ulcers, and various disorders involving motility, secretion, and absorption in the gastrointestinal tract; in the respiratory area, they may be beneficial in the therapy of bronchial asthma and other diseases involving bronchoconstriction; in hematology, they may have utility as anti-clotting agents in diseases such as venous thrombosis, thrombotic coronary occlusion and other diseases involving thrombi; in circulatory diseases they may have therapeutic utility in hypertension, peripheral vasopathies, and cardiac disorders.

In general, the natural prostaglandins affect smooth muscle regardless of origin in mammalian systems both in vivo and in vitro. This activity allows a rapid bioassay of prostaglandin derivatives or analogues by use of isolated muscle strips in vitro. (Cf. Bergstrom et al., Pharmacol. Rev., 20:1[1968]; Ferreira and Vane, Nature, 216:868 [1961].)

The field to which this invention pertains is discussed in the following references: The Prostaglandins, Vol. I., P. Ramwell, Ed., New York, Plenum Press, 1973; Ann. N.Y. Acad. Sci., 180:1–568 (1971); and Higgins and Braunwald, J. Am. Med. Assn., 53:92–112 (1972).

DESCRIPTION OF THE PRIOR ART 11-substituted $PGE_2$ and $PGF_{2\alpha}$ compounds, not related to those of the present invention, have been disclosed by Grudzinskas and Weiss, Tetrahedron Letters, No. 2, pp. 141–144, 1973. In the latter publication the substituents at $C_{11}$ of $PGE_2$ include: methyl, vinyl, carboxyl, amido, diethylmalonyl, methylthio, acetylthio, nitromethyl, and cyano. The only $PGF_{2\alpha}$ derivative reported is 11-cyano-$PGF_{2\alpha}$.

SUMMARY

The subject matter of this invention is a series of 11α-substituted -11-desoxy-prostaglandin derivatives of the E- and F-types having the formula

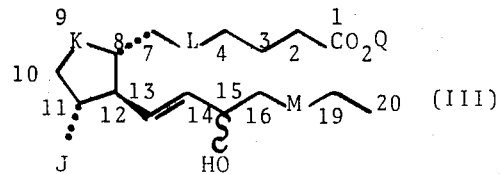

wherein:

J is phenyl, loweralkylphenyl, loweralkoxyphenyl, fluorophenyl, chlorophenyl, trifluoromethylphenyl biphenylyl, phenoxyphenyl, norbornyl, cycloalkyl of 3 to 8 carbon atoms, spiroalkyl of 5 to 13 carbon atoms, alkenyl of 3 to 8 carbon atoms, or 3-hydroxy-1-alkenyl of 3 to 8 carbon atoms.

K is a carbonyl or carbinol group, the latter of which is in the alpha-conformation;

L and M are ethylene or vinylene groups;

Q is hydrogen, loweralkyl, or a nontoxic cation; and, wherever used, the prefix "lower-" denotes 1 to 3 carbon atoms.

In III, a dotted line (....) represents the alpha -configuration (i.e., a covalent bond projecting below the reference carbon atom), while a wedge-shaped line (◄) indicates the beta-configuration (i.e., a covalent bond projecting above the reference carbon atom). A serpentine line (∽) means either the alpha- or the beta-configuration. The Arabic numerals at various carbon atoms of III follow the conventional numbering sequence utilized to identify carbon atoms in prostanoic acid or in natural prostaglandins.

The hydroxyl group at $C_{15}$, can be in the alpha- or beta-configurations.

When K is carbonyl, III represents derivatives of prostaglandins of the E-class: thus when L and M are both ethylene, III represents $PGE_1$ analogues; where L is vinylene and M is ethylene, $PGE_2$ derivatives are represented; and where both L and M are vinylene, $PGE_3$ analogues are depicted. On the other hand, when K is carbinol, III is representative of prostaglandins of the F-type, and the corresponding permutations of L and M described above provide structures of $PGF_{1\alpha}$, $PGF_{2\alpha}$, and $PGF_{3\alpha}$.

When J is a (substituted)phenyl group, the substituent can be on the para-, ortho-, or meta-position of the phenyl moiety. Thus, for example, when J is fluorophenyl, J can be p-fluorophenyl, m-fluorophenyl or o-fluorophenyl.

When J is a cycloalkyl group, the latter can be cyclopropyl, cyclobutyl, cyclopentyl, cyclohexyl, cycloheptyl, or cyclooctyl.

When J is a spiroalkyl group, this group can be spiro(3.3)heptyl, spiro(3.4)octyl, spiro(4.4)nonyl, spiro(5.3) nonyl, spiro(4.5)decyl, spiro(6.3)decyl, spiro(5.5)undecyl, spiro(6.4)undecyl, spiro(7.3)undecyl, spiro(5.6)dodecyl, spiro(7.4)dodecyl, spiro(8.3)dodecyl, spiro(6.6)tridecyl, spiro(5.7)tridecyl, spiro(4.8)-tridecyl, or spiro(3.9) tridecyl.

When J is a 1-alkenyl group of 3 to 8 carbon atoms, J can be a straight or branched alkenyl group. 1-octenyl, 6-methyl-1-heptenyl, 5-methyl-1-heptenyl, 4-methyl-1-heptenyl, 3-methyl-heptenyl, 4-ethyl-1-hexenyl, 3-ethyl-1-hexenyl, 5,5-dimethyl-hexenyl, 4,4-dimethyl-1-hexenyl, and 3,3,-dimethyl-1-hexenyl, or 1-propenyl.

When J is a 3-hydroxy-1-alkenyl of 3 to 8 carbon atoms, the latter can be 6-methyl-3-hydroxy-1-heptenyl, 4-methyl-3-hydroxy-1-heptenyl, 3-methyl-3-hydroxy-1-peptenyl, 4-ethyl-3-hydroxy-1hexenyl, 3-ethyl-3-hydroxy-1hexenyl, 4-methyl-3-hydroxy-1-pentenyl, or 3-hydroxy-1-propenyl.

Q can be hydrogen, methyl, ethyl, propyl, sodium or potassium.

The following are illustrative examples of III:
1. 11α-phenyl-11-desoxy-$PGE_1$, -$PGE_2$, -$PGE_3$, -$PGF_{1\alpha}$, -$PGF_{2\alpha}$, and -$PGF_{3\alpha}$.
2. 11α-(p-propyl)phenyl-11-desoxy-$PGE_1$, -$PGE_2$, -$PGE_3$, -$PGF_{1\alpha}$, -$PGF_{2\alpha}$, and -$PGF_{3\alpha}$.
3. 11α-(m-ethyl)phenyl-11-desoxy-$PGE_1$, -$PGE_2$, $PGE_3$, -$PGF_{1\alpha}$, -$PGF_{2\alpha}$, and -$PGF_{3\alpha}$.
4. 11α-(o-methyl)phenyl-11-desoxy-$PGE_1$, -$PGE_2$, -$PGE_3$, -$PGF_{1\alpha}$, -$PGF_{2\alpha}$, -$PGF_{3\alpha}$.
5. 11α-(p-propoxy)phenyl-11-desoxy-$PGE_1$, -$PGE_2$, -$PGE_3$, -$PGF_{1\alpha}$, -$PGF_{2\alpha}$, and -$PGF_{3\alpha}$.
6. 11α-(m-methoxy)phenyl-11-desoxy-$PGE_1$, -$PGE_2$, -$PGE_3$, -$PGF_{1\alpha}$, -$PGF_{2\alpha}$, and -$PGF_{3\alpha}$.
7. 11α-(o-ethoxy)phenyl-11-desoxy-$PGE_1$, -$PGE_2$, -$PGE_3$, -$PGF_{1\alpha}$, -$PGF_{2\alpha}$, and $PGF_{3\alpha}$.
8. 11α-(p-fluoro)phenyl-11-desoxy-$PGE_1$, -$PGE_2$, -$PGE_3$, -$PGF_{1\alpha}$, $PGF_{2\alpha}$, and -$PGF_{3\alpha}$.
9. 11α-(p-chloro)phenyl-11-desoxy-$PGE_1$, -$PGE_2$, -$PGE_3$, -$PGF_{1\alpha}$, -$PGF_{2\alpha}$, and -$PGF_{3\alpha}$.
10. 11α-(m-chloro)phenyl-11-desoxy-$PGE_1$, -$PGE_2$, -$PGE_3$, -$PGF_{1\alpha}$, -$PGF_{2\alpha}$, and -$PGF_{3\alpha}$.
11. 11α-(o-fluoro)phenyl-11-desoxy-$PGE_1$, -$PGE_2$, -$PGE_3$, -$PGF_{1\alpha}$, -$PGF_{2\alpha}$, and -$PGF_{3\alpha}$.
12. 11α-cyclobutyl-11-desoxy-$PGE_1$, -$PGE_2$, -$PGE_3$, -$PGF_{1\alpha}$, -$PGF_{2\alpha}$, and -$PGF_{3\alpha}$.
13. 11α-cyclopentyl-11-desoxy-$PGE_1$, -$PGE_2$, -$PGE_3$, -$PGF_{1\alpha}$, -$PGF_{2\alpha}$, and -$PGF_{3\alpha}$.
14. 11α-cyclohexyl-11-desoxy-$PGE_1$, -$PGE_2$, -$PGE_3$, -$PGF_{1\alpha}$, -$PGF_{2\alpha}$, and -$PGF_3$.
15. 11α-cycloheptyl-11-desoxy-$PGE_1$, -$PGE_2$, $PGE_3$, -$PGF_{1\alpha}$ -$PGF_{2\alpha}$, and -$PGF_{3\alpha}$.
16. 11α-cyclooctyl-11-desoxy-$PGE_1$, -$PGE_2$, -$PGE_3$, -$PGF_{1\alpha}$, -$PGF_{2\alpha}$, and -$PGF_{3\alpha}$.
17. 11α-spiro(3.3)heptyl-11-desoxy-$PGE_1$, -$PGE_2$, -$PGE_3$, -$PGF_{1\alpha}$, -$PGF_{2\alpha}$, and -$PGF_{3\alpha}$.
18. 11α-spiro(3.4)octyl-11-desoxy-$PGE_1$, -$PGE_2$, -$PGE_3$, -$PGF_{1\alpha}$, -$PGF_{2\alpha}$, -$PGF_{3\alpha}$.
19. 11α-spiro(4.4)nonyl-11-desoxy-$PGE_1$, -$PGE_2$, -$PGE_3$, -$PGF_{1\alpha}$, -$PGF_{2\alpha}$, and -$PGF_{3\alpha}$.
20. 11α-spiro(5.3)nonyl-11-desoxy-$PGE_1$, -$PGE_2$, -$PGE_3$, -$PGF_{1\alpha}$, -$PGF_{2\alpha}$, and -$PGF_{3\alpha}$.
21. 11α-spiro(4.5)decyl-11-desoxy-$PGE_1$, -$PGE_2$, -$PGE_3$, -$PGF_{1\alpha}$, -$PGF_{2\alpha}$, and $PGF_{3\alpha}$.
22. 11α-spiro(6.3)decyl-11-desoxy-$PGE_1$, -$PGE_2$, -$PGE_3$, -$PGF_{1\alpha}$, $PGF_{2\alpha}$, and -$PGF_{3\alpha}$.
23. 11α-spiro(5.5)undecyl-11-desoxy-$PGE_1$, -$PGE_2$, -$PGE_3$, -$PGF_{1\alpha}$, -$PGF_{2\alpha}$, and -$PGF_{3\alpha}$.
24. 11α-spiro(6.4)undecyl-11-desoxy-$PGE_1$, -$PGE_2$, -$PGE_3$, -$PGF_{1\alpha}$, -$PGF_{2\alpha}$, and -$PGF_{3\alpha}$.
25. 11α-spiro(7.3)undecyl-11-desoxy-$PGE_1$, -$PGE_2$, -$PGE_3$, -$PGF_{1\alpha}$, -$PGF_{2\alpha}$, and -$PGF_{3\alpha}$.
26. 11α-spiro(5.6)dodecyl-11-desoxy-$PGE_1$, -$PGE_2$, -$PGE_3$, -$PGF_{1\alpha}$, -$PGF_{2\alpha}$, and -$PGF_{3\alpha}$.
27. 11α-spiro(7.4)dodecyl-11-desoxy-$PGE_1$, -$PGE_2$, -$PGE_3$, -$PGF_{1\alpha}$, -$PGF_{2\alpha}$, and -$PGF_{3\alpha}$.
28. 11α-spiro(8.3)dodecyl-11-desoxy-$PGE_1$, -$PGE_2$, -$PGE_3$, -$PGF_{1\alpha}$, -$PGF_{2\alpha}$, and -$PGF_{3\alpha}$.
29. 11α-spiro(6.6)tridecyl-11-desoxy-$PGE_1$, -$PGE_2$, -$PGE_3$, -$PGF_{1\alpha}$, -$PGF_{2\alpha}$, and -$PGF_{3\alpha}$.
30. 11α-spiro(5.7)tridecyl-11-desoxy-$PGE_1$, -$PGE_2$, -$PGE_3$, -$PGF_{1\alpha}$, -$PGF_{2\alpha}$, and -$PGF_{3\alpha}$.
31. 11α-spiro(4.8)tridecyl-11-desoxy-$PGE_1$, -$PGE_2$, -$PGE_3$, -$PGF_{1\alpha}$, -$PGF_{2\alpha}$, and -$PGF_{3\alpha}$.
32. 11α-spiro(3.9)tridecyl-11-desoxy-$PGE_1$, -$PGE_2$, -$PGE_3$, -$PGF_{1\alpha}$, -$PGF_{2\alpha}$, and -$PGF_{3\alpha}$.
33. 11α-(1-octenyl)-11-desoxy-$PGE_1$, -$PGE_2$, -$PGE_3$, -$PGF_{1\alpha}$, -$PGF_{2\alpha}$, and -$PGF_{3\alpha}$.
34. 11α-(6-methyl-1-heptenyl)-11-desoxy-$PGE_1$, -$PGE_2$, -$PGE_3$, -$PGF_{1\alpha}$, -$PGF_{2\alpha}$, and -$PGF_{3\alpha}$.
35. 11α-(5-methyl-1-heptenyl)-11-desoxy-$PGE_1$, -$PGE_2$, -$PGE_3$, -$PGF_{1\alpha}$, -$PGE_{2\alpha}$, and -$PGF_{3\alpha}$.
36. 11α-(4-methyl-1-heptenyl)-11-desoxy-$PGE_1$, -$PGE_2$, -$PGE_3$, -$PGF_{1\alpha}$, -$PGF_{2\alpha}$, and -$PGF_{3\alpha}$.
37. 11α-(4-ethyl-1-hexenyl)-11-desoxy-$PGE_1$, -$PGE_2$, -$PGE_3$, -$PGF_{1\alpha}$, -$PGF_{2\alpha}$, and -$PGF_{3\alpha}$.
38. 11α-(3-ethyl-1-hexenyl)-11-desoxy-$PGE_1$, -$PGE_2$, -$PGE_3$, -$PGF_{1\alpha}$, -$PGF_{2\alpha}$, and -$PGF_{3\alpha}$.
39. 11α-(5,5-dimethyl-1-hexenyl)-11-desoxy-$PGE_1$, -$PGE_2$, -$PGE_3$, -$PGF_{1\alpha}$, -$PGF_{2\alpha}$, and $PGF_{3\alpha}$.
40. 11α-(4,4-dimethyl-1-hexenyl)-11-desoxy-$PGE_1$, -$PGE_2$, -$PGE_3$, -$PGF_{1\alpha}$, -$PGF_{2\alpha}$, and $PGF_{3\alpha}$.

41. 11α-(3,3-dimethyl-1-hexenyl)-11-desoxy-PGE₁, PGE₂, -PGE₃, -PGF$_{1\alpha}$, -PGF$_{2\alpha}$, and -PGF$_{3\alpha}$.
42. 11α-(1-propenyl)-11-desoxy-PGE₁, -PGE₂, -PGE₃, -PGF$_{1\alpha}$, -PGF$_{2\alpha}$, and -PGF$_{3\alpha}$.
43. 11α-(2-propenyl)-11-desoxy-PGE₁, -PGE₂, -PGE₃, -PGF$_{1\alpha}$, -PGF$_{2\alpha}$, and -PGF$_{3\alpha}$.
44. 11α-(6-methyl-3-hydroxy-1-heptenyl)-11-desoxy-PGE₁, -PGE₂, -PGE₃, -PGF$_{1\alpha}$, -PGF$_{2\alpha}$, and -PGF$_{3\alpha}$.
45. 11α-(4-methyl-3-hydroxy-1-heptenyl)-11-desoxy-PGE₁, -PGE₂, -PGE₃, -PGF$_{1\alpha}$, -PGF$_{2\alpha}$, and -PGF$_{3\alpha}$.
46. 11α-(3-methyl-3-hydroxy-1-pentenyl)-11-desoxy-PGE₁, -PGE₂, -PGE₃, -PGF$_{1\alpha}$, -PGF$_{2\alpha}$, -PGF$_{3\alpha}$.
47. 11α-(4-ethyl-3-hydroxy-1-hexenyl)-11-desoxy-PGE₁, -PGE₂, -PGE₃, -PGF$_{1\alpha}$, -PGF$_{2\alpha}$, and -PGF$_{3\alpha}$.
48. 11α-(4-ethyl-3-hydroxy-1-hexenyl)-11-desoxy-PGE₁, -PGE₂, -PGE₃, -PGF$_{1\alpha}$, -PGF$_{2\alpha}$, and -PGF$_{3\alpha}$.
49. 11α-(4-methyl-3-hydroxy-1-pentenyl)-11-desoxy-PGE₁, -PGE₂, -PGE₃, -PGF$_{1\alpha}$, -PGF$_{2\alpha}$, and -PGF$_{3\alpha}$.
50. 11α-(3-hydroxy-1-propenyl)-11-desoxy-PGE₁, -PGE₂, -PGE₃, -PGF$_{1\alpha}$, -PGF$_{2\alpha}$, and -PGF$_{3\alpha}$.
51. 11α-biphenylyl-11-desoxy-PGE₁, -PGE₂, -PGE₃, -PGF$_{1\alpha}$, -PGF$_{2\alpha}$, and -PGF$_{3\alpha}$.
52. 11α-(p-phenoxy)phenyl-11-desoxy-PGE₁, -PGE₂, -PGE₃, -PGF$_{1\alpha}$, -PGF$_{2\alpha}$, and -PGF$_{3\alpha}$.
53. 11α-(2-norbornyl)-11-desoxy-PGE₁, -PGE₂, -PGE₃, -PGF$_{1\alpha}$, -PGF$_{2\alpha}$, and -PGF$_{3\alpha}$.

The 11α-phenyl- and 11α-(substituted)phenyl-11-desoxy -derivatives of PGE₁, PGE₂ and PGE₃ are prepared from the corresponding 15α-ethoxyethoxy-PGA-methyl ester according to the method of Sih et al. (J. Am. Chem. Soc., 95: 1676 [1973]):

(1) $CuC \equiv C-(CH_2)_2-CH_3 \cdot 2[(CH_3)_2N]_3PCuI$ (V) or

[(CH₃)₂N]₃CuI (VI)

(2) 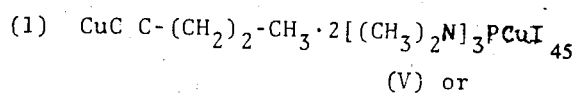

(VII)

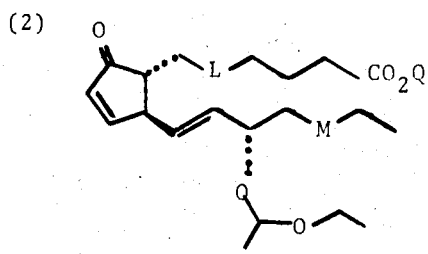

(VIII)

(3) $CH_3CO_2H$, $H_2O$; THF (4) $H_2O$, THF, NaOH

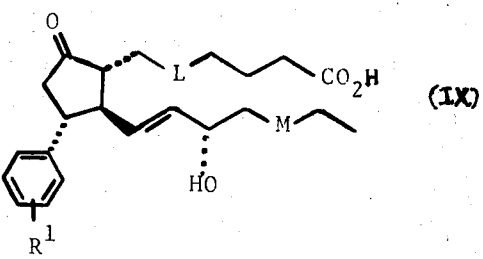

(IX)

In the above reaction scheme, the starting material IV is readily prepared from the corresponding bromo- or iodo-derivatives which are commercially available; in IV, R¹ can be hydrogen, loweralkyl of 1 to 3 carbon atoms, loweralkoxy of 1 to 3 carbon atoms, fluoro, chloro, trifluoromethyl, phenyl or phenoxy. Intermediate V is prepared by reacting cuprious-n-propyl acetylide (prepared according to Castro et al., J. Org. Chem., 31: 4071 [1966]) and hexamethylphosphorus triamide copper iodide, VI. Compound VI is prepared as follows: (1) add 18.39 g of purified CuI (Inorg. Synth., 7: 9 [1963]) to 177 g KI in 135 ml. H₂O and stir with activated charcoal (Norite); (2) filter the solution through infusorial earth (Celite) and add 14.5 g (0.089 mole) of hexamethylphosphorous triamide (commercially available) under argon atmosphere; (3) filter, wash with aqueous KI and H₂O; (4) dissolve product in dry ether, filter, remove ether in vacuo to obtain 13.85 g hexamethylphosphorous triamide copper (I) iodide:NMR (COCl₃): singlet, δ 2.65. Compound VII, 15α-ethoxyethoxy-PGA-methyl ester is prepared from 15-α-hydroxy-PGA, which is available from coral extracts or which can be synthesized according to the Corey or Sih procedures (Corey et al., J. Am. Chem. Soc., 91: 5675 [1969]; Sih et al., J. Am. Chem. Soc., 95: 1676 [1973]).

The ethoxyethoxy group of VII is introduced by the procedure of Sih et al. (Tetrahedron Letters, No. 24, 2435 [1972]). The conditions for the reactions IV → VIII and VIII → IX are described by Sih et al. in the last cited reference. In the reaction VIII → IX, step (3) and (4) relate to the removal of the ethoxyethoxy group and of the ester group, respectively. In VIII, IX and X, the symbols L and M have the same definition as in III, supra.

The 11α-phenyl- and 11α-(substituted)phenyl-11-desoxy -PGF$_{1\alpha}$, -PGF$_{2\alpha}$, and -PGF$_{3\alpha}$ derivatives are prepared from IX according to the following reaction (Cf. Anderson, Am. N.Y. Acad. Sci., 180: 17 [1971]):

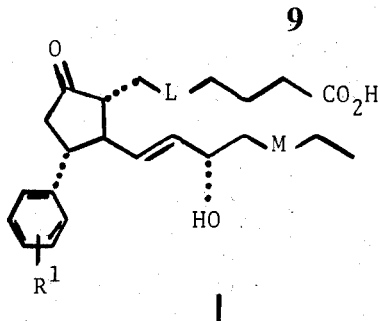

↓ NaBH₄; CH₃OH

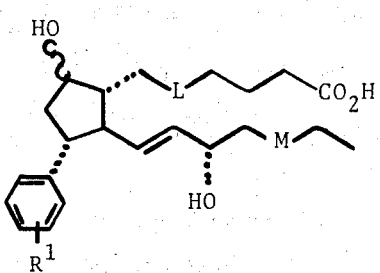

In X, the symbols L and M have been defined above in III.

The 11α-cycloalkyl- and 11α-spirocycloalkyl-11-desoxy -PGE₁, -PGE₂, and -PGE₃ analogues are synthesized by reacting the corresponding 15α-ethoxyethoxy-PGA compounds, VII, with appropriate organoboranes according to the reaction reported by H. C. Brown and G. W. Kabalka (J. Am. Chem. Soc., 93: 714 [1970]).

$$R^2 \quad (XI)$$

↓ THF, BH₃

$$(R^2)_3\text{-B} \quad (XII)$$

(1) ↓

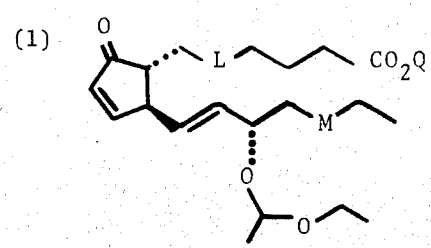

(VII)

(2) ↓ O₂

ENOL BORINATE INTERMEDIATE (IX)

(3) H₂O
(4) CH₃CO₂H; THF; H₂O
(5) H₂O, THF, NaOH

↓

(X)

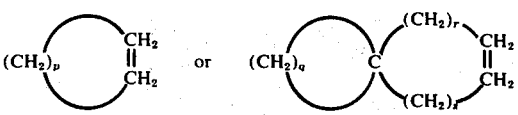

(XIII)

In the above reaction sequence R² (Formula XI) can be cyclopropene, cyclobutene, cyclopentene, cyclohexene, cycloheptene, cyclooctene, cyclononene, 2-norbornene, spiro (3.3)heptene, spiro(3.4)hept-1-ene, spiro(3.4)hept-6-ene, spiro(4.4)non-2-ene, spiro(5.3)-non-1-ene, spiro(5.3)non-6-ene, spiro(4.5)dec-2-ene, spiro(4.5)dec-7-ene, spiro(6.3)dec-1-ene, spiro(6.3)-dec-5-ene, spiro(6.3)dec-6-ene, spiro(5.5)undec-1-ene, spiro(5.5)undec-2-ene, spiro(6.4)undec-2-ene, spiro(6.4)undec-7-ene, spiro(7.3)undec-1-ene, spiro(7.3)undec-5-ene, spiro(7.3)undec-6-ene, spiro(7.-3)undec-7-ene, spiro(7.3)undec-8-ene, spiro(5.6)dodec-1-ene, spiro(5.6)dodec-2-ene, spiro(5.6)dodec-7-ene, spiro(5.6)dodec-8-ene, spiro(5.6)dodec-9-ene, spiro(7.4)dodec-1-ene, spiro(7.4)dodec-2-ene, spiro(7.4)dodec-6-ene, spiro(7.4)dodec-7-ene, spiro(7.4-)dodec-8-ene, spiro(6.6)tridec-2-ene, spiro(6.6)tridec-3-ene, spiro(5.7)tridec-1-ene, sprio(5.7)tridec-2-ene, spiro(5.7)tridec-7-ene, spiro(5.7)tridec-8-ene, spiro(5.7)tridec-8-ene. In general, R² (XI) can be:

wherein p is an integer having a value of from 0 to 6, q is an integer having a value of from 3 to 7, and r and s are integers having a value of from 0 to 3.

Reaction XI → XII represents the formation of a trialkylborane as described by Brown and Kabalka. In the reaction XII → XIII, step (2) is the oxygen induced 1,4 addition of the trialkylborane XII to the α, β-unsaturated carbonyl intermediate, VII, resulting in an intermediate enol borinate. Hydrolysis of the latter, step (3), yields the 11α-substituted-15-α-ethoxyethoxy-PGE or PGF derivative. Steps (4) and (5) involve cleavage of the ethoxyethoxy group and the alkyl ester, respectively, described above.

Compounds XI, easily are converted into the corresponding PGF analogues by treatment with $NaBH_4$ in methanol to convert the $C_9$ carbonyl group to a carbinol group.

The 11α-(alkenyl)- and 11α-(3-hydroxy-1-alkenyl)-11-desoxy-$PGE_1$, -$PGE_2$ and -$PGE_3$ compounds (see XV, below) are synthesized from the corresponding -15αethoxyethoxy-PGA derivatives by utilizing the method of Sih et al. (J. Am. Chem. Soc., 95:1676 [1973]).

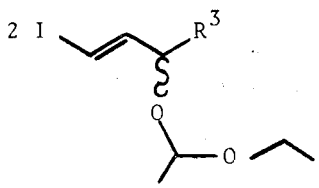
(XIV)

(1) <u>t</u>-butyllithium (2) $[(CH_3)_2N]_3PCuI$     (VI)

(3)

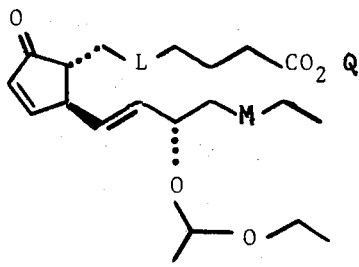
(VII)

(4) $CH_3CO_2H$, THF, $H_2O$ (5) $H_2O$, THF, NaOH

↓

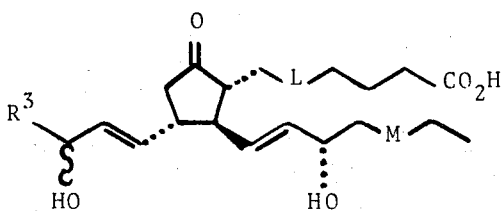
(XV)

In XIV, $R^3$ can be a straight-chain or branched alkyl moiety of 1 to 5 carbon atoms. The 3-ethoxyethoxy group is introduced to the corresponding 3-hydroxy-substituted analogue of VII according to the method outlined by Sih et al. (Tetrahedron Letters, No. 24, 2435 [1972]). In the reaction XIV → XV, steps (1) through (5) have been described above. In VII and XV, the symbols L and M have the same definition as in III.

XIV may be

$R^4$ being branched or straight chain alkyl of 1 to 6 carbon atoms.

Compounds III of this invention are useful analogues of the natural E- and F-type prostaglandins and stimulate isolated smooth muscle of diverse tissues from experimental animals. In vitro smooth muscle assays to determine activity of prostaglandin analogues are widely utilized in the field. See, for example, the publication by Bundy et al., Ann. N.Y. Acad. Sci., 180:76 (1971). The use of in vitro isolated smooth muscle preparations for the assay of prostaglandin activity is discussed by Bergstrom et al. (Pharmacol. Rev., 20:1 [1968]).

Detailed results are provided in Example 4, below.

DESCRIPTION OF THE PREFERRED EMBODIMENTS

EXAMPLE 1

11-CYCLOHEXY-11-DESOXY-PROSTAGLANDIN DERIVATIVES 1.10 mmol of 1M tetrahydrofuran-triborane was injected into a 10 ml round-bottom flask equipped with a serum cap, magnetic stirrer, condenser and argon inlet. 3.3 mmol of cyclohexene (271 mg) was introduced into the flask and the reaction mixture was stirred for 3.0 hours at 45°–55° C. 0.0036 ml of water and 1.0 mmol (466 mg) of 15α-ethoxyethoxy-$PGA_2$-methyl ester in 1.0 ml of tetrahydrofuran (THF) was then introduced into the flask. The resulting mixture was stirred for 15 min. at 25° C. while air was passed over the solution at a rate of 1.0 ml/min. The reaction mixture was poured into 20% aqueous $NH_4Cl$ and extracted with ether. The ether extracts were washed with 2% (V/V) $H_2SO_4/H_2O$ and saturated NaCl. After drying and filtration, 550 mg of a yellow oil was obtained. NMR ($CDCl_3$) revealed no signals attributable to the 15-ethoxyethoxy-$PGA_2$-methyl ester. The ethoxyethoxy protecting groups were hydrolyzed with 11.5 ml of acetic acid/water 61/35 and 1.0 ml of THF for 19 hrs at 25° C. 373 mg of a yellow oil was obtained after washing with 2% saturated aqueous $NaHCO_3$ and saturated aqueous NaCl. NMR ($CDCl_3$) revealed no signals attributable to

of the protecting group. The methyl ester was hydrolyzed by reacting the product with 5.51 ml of 1N NaOH and 5.51 ml. THF with stirring at 25° C. After extraction and washing, 145 mg of a yellow oil was obtained which was combined with products from two other identically performed experiments; the total being 731 mg. After chromatography, 130 mg of a yellow oil, 11α-cyclohexyl-11-desoxy-$PGE_2$, was obtained.

ANALYSIS: $[\alpha]_D$:

−28.1° ± 0.3° (C = 1.00, $CHCl_3$)

MS:
418 (molecular ion)
NMR (CDCl$_3$):
  δ 6.90, m, 2H, CO$_2$H, OH
  δ 5.45, m, 2H, trans-olefinic H
  δ 5.30, m, 2H, cis-olefinic H
  δ 4.10, m, 1H, CHOH
  δ 0.85, t, 3H, -CH$_2$-CH$_3$
IR:
  $\lambda_{max}^{CHCl_3}$ 2.78μ, 5.78μ, 5.85μ

Substitution of 15α-ethoxyethoxy-PGA$_1$ methyl ester and 15α-ethoxyethoxy-PGA$_3$ methyl ester in lieu of 15α-ethoxyethoxy-PGA$_2$ methyl ester in the above procedure yields the 11-cyclohexyl-11-desoxy-PGE$_1$ and PGE$_2$ derivatives. The corresponding 11-cyclohexyl-11-desoxy-PGF$_{1\alpha}$, -PGF$_{2\alpha}$ and -PGF$_{3\alpha}$ derivatives are prepared from the appropriate 11-cyclohexyl-11-desoxy-prostaglandin E compounds by reaction with NaBH$_4$ in methanol.

By using cyclooctene and cyclopentene instead of cyclohexene in the above procedure the corresponding 11-cyclooctane- and 11-cyclopentane-11-desoxy-substituted PGE$_1$, PGE$_2$, and PGE$_3$, are obtained, which are easily converted into the corresponding -PGF$_{1\alpha}$, -PGF$_{2\alpha}$, and -PGF$_{3\alpha}$ analogues.

EXAMPLE 2

11α-PHENYL-11-DESOXY-PROSTAGLANDIN DERIVATIVES 2.70 ml (14.90 mmol) hexamethylphophorous triamide was added to a slurry of 960 mg (7.35 mmol) of cuprous-n-propylacetylide (Cf. J. Org. Chem., 31:4071 [1966]) in 20 ml of anhydrous ether with stirring at 25° C. under argon atmosphere. This reaction mixture was stirred until clear (15 min.) and then cooled to −78° C. Subsequently 4.90 ml of 1.50M phenyl lithium in ether/hexane was slowly added with stirring at −78° C., and 2.70 g (4.44 mmol) of 15α-ethoxyethoxy-PGA$_2$-methyl ester in 20 ml of anhydrous ether was added thereafter. The reaction mixture was stirred for 15.0 minutes at −78° C. and then slowly warmed to 0° C. in an ice-salt water bath over an one hour interval. The reaction mixture was stirred for an additional 30 min. at 25° C. The mixture was poured into cold 20% aqueous (NH$_4$)$_2$SO$_4$, and extracted three times with ether. The ether extracts were washed with cold 2% (V/V) H$_2$SO$_4$/H$_2$O and filtered through infusorial earth (Celite). The filtrate was washed with 5% NaHCO$_3$ and subsequently dried over magnesium sulfate, yielding 3.16 g of a green oil. NMR(CDCl$_3$) analysis revealed: δ7.28, singlet, phenyl-H; δ3.67, singlet, CO$_2$CH$_3$; δ5.40, multiplet, cis- and trans-olefinic H.

The C$_{15}$ hydroxyl protecting group was removed by reacting the crude reaction mixture with 65 ml of acetic acid/water (65/35) and 6.50 ml of THF for 1 hour at 25° C. This mixture was poured into 100 ml water and extracted 3 times with dichloromethane. The dichloromethane layer was shaken into aqueous sodium bicarbonate, saturated aqueous sodium chloride, and then dried, filtered and evaporated. 2.63 g of a green oil was recovered which was stirred with 36 ml of 1N NaOH and 36 ml of THF for 21 hours at 25° C. The THF was removed by evaporation at 35° C., and the residue was poured into 50 ml H$_2$O. This mixture was extracted three times with 50 ml of ether/ethyl acetate (1/1). The organic layers were combined and extracted twice with water. The aqueous layers were combined, acidified with concentrated HCl and extracted three times with ether. The ether layers were combined, washed with saturated aqueous NaCl, dried over anhydrous MgSO$_4$ and filtered. 2.30 g of an orange oil was obtained. This material was chromatographed on silicic acid/Celite (85:15). Elution with benzene/ethyl acetate gradient afforded 1.10 g of a yellow oil (60.2%) yield: 11α-phenyl-11-desoxy-PGE$_2$.

ANALYSIS: [α]$^D$:
  −69.00° ± 0.2° (c = 0.99 methanol)
NMR(CDCl$_3$):
  δ 7.2, singlet, phenyl-H, 5H
  δ 5.45, multiplet, cis- and trans-olefinic-H, 4H
  δ 6.77, broad singlet, CO$_2$H, −OH, 2H.
IR(CHCl$_3$):
  $\lambda_{max}$ 5.84μ, 5.78μ, 2.78μ, 2.94μ.

Use of 15α-ethoxyethoxy-PGA$_1$-methyl ester and 15α-ethoxyethoxy-PGA$_3$-methyl ester in place of the corresponding PGA$_2$ derivative in the above example yields the corresponding 11-phenyl-11-desoxy-substituted PGE$_1$ and PGE$_3$ derivatives.

11α-phenyl-11-desoxy-substituted PGF$_{1\alpha}$, PGF$_{2\alpha}$, and PGF$_{3\alpha}$ derivatives are synthesized from the corresponding 11-α-phenyl-11-desoxy-PGE$_1$, -PGE$_2$ and -PGE$_3$ by treatment with NaBH$_4$ in methanol.

11α-(ethyl)phenyl, 11-α-(ethoxy)phenyl, -11α-(fluoro)phenyl-, 11-α-(chloro)phenyl-, and 11-α-trifluoromethylphenyl- substituted 11-desoxy-PGE$_1$, -PGE$_2$, -PGE$_3$, -PGF$_{1\alpha}$, -PGF$_{2\alpha}$ and -PGE$_{3\alpha}$ are prepared by utilization of p-chlorophenyl, and p-ethoxyphenyl-, p-fluorophenyl, p-chlorophenyl, and p-trifluoromethylphenyl-lithium instead of the phenyl-lithium utilized in the example.

EXAMPLE 3

11α-(TRANS-3 -β-HYDROXY-1-ALKENYL)-11-DESOXY-PGE$_2$ 2.50 g (8.40 mmol) of trans-4-methyl-3α-ethoxyethoxy-1-iodopentene was dissolved in 57 ml of anhydrous ether and cooled to −78° C. with stirring under argon atmosphere. To this solution 13.7 ml of 1.23 N t-butyllithium in pentane was injected. The resulting solution was stirred for 2.75 hours at −78° C. under argon atmosphere, yielding the lithio-anion, 1-lithio-trans-4-methyl-3α-ethoxyethoxy-1-pentene. The lithio-anion was added to a solution of 0.44 g hexamethylene-phosphorous triamide copper iodide in 50 ml of anhydrous ether at −78° C. under argon. This yellow mixture was stirred for 15 minutes at −78° C. Then 1.97 g (4.22 mmol) of 15α-ethoxyethoxy-PGA$_2$-methyl ester in 11.5 ml ether was added dropwise and the reaction mixture was stirred at −70° C. for 15 min. The mixture was then slowly warmed to 0° C. over a period of 1.5 hr. by use of an ice water and salt bath, and stirred for 0.5 hr. The mixture was then brought to 25° C. and stirred for an additional 0.5 hr. The mixture was then processed with a 20% aqueous NH$_4$Cl/NH$_4$OH solution and 3.35 g of an orange oil was obtained. NMR(CDCl$_3$) analysis revealed: δ 3.65, singlet, CO$_2$CH$_3$; δ ≅5.45, multiplet, olefinic-H; and no absorption due to olefinic protons on the cyclopen-tenone in the PGA$_2$ starting material. The ethoxyethoxy groups were hydrolyzed by reacting with 70 ml of 65/35 acetic acid/water and 7.0 ml THF for 17 hours at 25° C. After processing, 3.30 g of an orange oil were obtained. NMR (CDCl$_3$) analysis showed no absorption in the δ 4.80 region. The methyl ester was hydrolyzed by reaction with 22 ml of 1N NaOH and 22 ml of THF for 19 hours at 25° C. under argon atmosphere. After processing 3.28 g of a red oil was obtained chromatographed in Silicic Acid and Celite (15%). 1.227 g (65.6%) of (−)-11α-(trans-4'-methyl-3'-β-hydroxy-1-pentenyl-11-desoxy-PGE$_2$ was obtained. NMR(CDCl$_3$) analysis: δ 3.95, multiplet, 2H, C$\underline{H}$OH; δ 5.45, multiplet, 6H, CO$_2$$\underline{H}$, -O$\underline{H}$. IR analysis: $\lambda_{max}^{CHCl_3}$ 2.68μ, 5.75μ, 5.85μ. Optical rotation: $[\alpha]^D 25°$ = 36.4 ± 02° (c = 1.0, CH$_3$OH). Mass spectoscopy: 416 (P$^+$- 18).

Substitution of

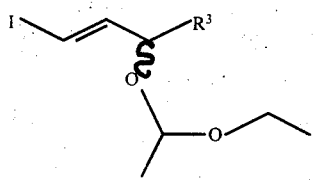

where R$^3$ is a straight or branched alkyl group yields other 11α-(trans-3β-hydroxyl-1-alkenyl)-11-desoxy-PGE$_2$ derivatives.

EXAMPLE 4

PROSTAGLANDIN ACTIVITY IN THE CASCADE ASSAY SYSTEM

The superfusion technique introduced by Gaddum (Brit. J. Pharmacol., 6:321 [1953]) consists of bathing an isolated tissue by a continuous dropwise application of a nutrient solution, rather than by submersion in a chamber filled with the solution. This procedure allows a greater sensitivity for biological assays, since test compounds are less diluted than in usual systems. An additional advantage is that a compound can be tested simultaneously in several structures by arranging the tissues in vertical succession to allow successive contact with the test material. This procedure has been designated the cascade system. The cascade has been specially useful for determination of prostaglandins (Ferreira and Vane, Nature, 216:868 [1967]).

A. Procedure

Rat stomach fundus. After sacrifice of the animal, the stomach was removed, the antrum cut transversely and the fundus cut in order to preserve the longitudinal muscle (Vane, Brit. J. Pharmacol., 12:344 [1957]).
Rat colon. The animal was sacrificed and a segment of ascending colon (2.0 − 2.5 cm long) was obtained (Regoli and Vane, Brit. J. Pharmacol., 23:351 [1964]).
Chick rectum. Chicks 3 to 10 days old were anesthetized with ether and the complete rectum was removed (Mann and West, Brit. J. Pharmacol., 5:173 [1950]).

One end of tissue preparations was tied to the bottom of a tissue chamber and the other to a force displacement transducer for tension recording. The chambers possessed an external jacket in which water at 37° C. is circulated. Preparations were placed one beneath the other and provision was made for bathing the three tissues successively with the same fluid.

Superfusion fluid.

Krebs bicarbonated solution bubbled with a mixture of 95% O$_2$ and 5% CO$_2$ and kept at 37° C. was applied dropwise over the preparations at a rate of 10 ml/min. The following antagonists were added to the solution. atropine (0.1 mcg/ml), phenoxy-benzamine (0.1 mcg/ml), propranolol (0.3 mcg/ml), methysergide (0.2 mcg/ml and brompheniramine (0.1 mcg/ml). The use of these antagonists in the nutrient eliminated the possibility of smooth muscle responses being due to stimulation of cholinergic, adrenergic, serotonin or histamine receptors.

Test Compounds.

Prostaglandin derivatives were diluted in order to administer concentrations ranging from 0.001 ng to 100 mcg. Concentrations were applied in a 0.5 ml volume. dropwise on the first structure. The relative position of the three tissues used did not influence the magnitude or pattern of responses.

B. Results

In the following table, Compound A is 11α-phenyl-11-desoxy-PGE$_2$, Compound B is (−)-11α-(trans-4'-methyl-3'-β-hydroxy-1-pentenyl)-11-desoxy-PGE$_2$, and Compound C is 11α-cyclohexyl-11-desoxy-PGE$_2$. In the table 0 indicates no response at the dose tested and a dash (−) indicates that the compound was not tested.

TABLE

| Compound | Tissue | gm tension/dose (mcgm) | | | | | | | | |
|---|---|---|---|---|---|---|---|---|---|---|
| | | $10^{-6}$ | $10^{-5}$ | $10^{-4}$ | $10^{-3}$ | 0.01 | 0.1 | 1.0 | 10 | 100 |
| A | Rat Stomach | — | — | — | 0.3 | 2.6 | 3.1 | 3.8 | 4.7 | 5.4 |
| | Rat Colon | — | — | — | 0 | 0 | 0 | 0 | 0 | 2.5 |
| | Chick Rectum | — | — | — | 0 | 0 | 0 | 0 | 0 | 1.25 |
| B | Rat Stomach | — | — | — | — | — | 0 | 0.4 | 1.0 | 1.6 |
| C | Rat Stomach | 1.1 | 2.2 | 2.2 | 2.3 | 2.0 | 2.5 | 2.9 | 2.6 | 2.6 |

What is claimed is:
1. A compound of the formula

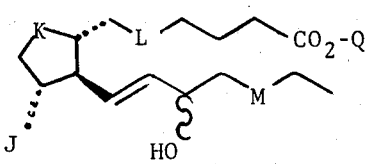

wherein:
J is selected from the group consisting of cycloalkyl of 3 to 8 carbon atoms, and 3-hydroxy-1-alkenyl of 3 to 8 carbon atoms;
K is carbonyl;
L and M respectively are vinylene and ethylene radicals; and,
Q is selected from the group consisting of hydrogen, loweralkyl of 1 to 3 carbon atoms, and a nontoxic cation.

2. A compound as in claim 1, (−)-11α-(trans-4'-methyl-3'-β-hydroxy-1-pentenyl)-11-desoxy-PGE$_2$.

3. A compound as in claim 1, 11-cyclohexyl-11-desoxy-PGE$_2$.

* * * * *